United States Patent [19]

Baker

[11] 4,302,421
[45] Nov. 24, 1981

[54] METHOD AND APPARATUS FOR FLUSHING A DELIVERY TUBE FOR AUTOMATIC LIQUID SAMPLE SUPPLY APPARATUS

[75] Inventor: Stephen J. Baker, Cambridge, England

[73] Assignee: Pye (Electronic Products) Limited, Cambridge, England

[21] Appl. No.: 123,858

[22] Filed: Feb. 22, 1980

[30] Foreign Application Priority Data

Feb. 27, 1979 [GB] United Kingdom ............... 06832/79

[51] Int. Cl.³ .................... G01N 35/06; G01N 1/14
[52] U.S. Cl. ................................. 422/64; 23/230 R; 73/864.16; 73/864.22; 422/63; 422/102
[58] Field of Search ............... 422/64, 63, 102, 104; 23/230 R; 73/425.6, 423 A; 141/130

[56] References Cited

U.S. PATENT DOCUMENTS 3,192,968  7/1965  Baruch et al. ............... 422/64 X
3,266,322  8/1966  Negersmith et al. ......... 422/64 X
3,430,495  3/1969  Burge ........................... 73/423 A
4,186,187  1/1980  Jahnsen et al. ............... 422/64

Primary Examiner—Ronald Serwin
Attorney, Agent, or Firm—Thomas A. Briody; Robert T. Mayer; Paul R. Miller

[57] ABSTRACT

An automatic sample supply apparatus is provided with a delivery tube which aspirates liquid samples from sample containers mounted on a turntable and delivers the samples to a dosing aperture of a graphite tube of an atomic absorption spectrophotometer or to the sample input of other analytical instruments. The turntable also carries at least one flushing discharge container which is of similar form to the sample container, but has an aperture in the side wall. When the turntable is indexed so that the delivery tube enters the flushing discharge container, a solenoid valve is opened to allow a flushing liquid from a container to flow through the delivery tube and into the flushing discharge container. The aperture in the wall of the flushing discharge container is dimensioned so that the flushing liquid will only flow through it when a given head of liquid exists above the top of the aperture.

17 Claims, 4 Drawing Figures

METHOD AND APPARATUS FOR FLUSHING A DELIVERY TUBE FOR AUTOMATIC LIQUID SAMPLE SUPPLY APPARATUS

The invention relates to an automatic liquid sample supply apparatus for sequentially supplying liquid samples to an associated analytical instrument, to a flushing discharge container for use in such apparatus in which a delivery tube for delivering liquid samples for analysis may be flushed between successive sample deliveries, and to a method of flushing a delivery tube in such apparatus incorporating such a container.

In flameless atomic absorption spectroscopy it has become increasingly desirable to automate the injection of successive samples into the dosing aperture of the graphite tube of an atomisation device. However, if the results of the analysis are to be useful it is necessary to minimise the possibility of sample carry-over, i.e. the sample substance must not contaminate the next analysis.

In apparatus for atomic absorption spectroscopy known from U.K. Pat. No. 1,492,515 successive samples are aspirated from a sample container by means of a single tubular member, which after each sample aspiration is then moved to an atomisation device and the aspirated sample is delivered into it, and a flushing stage is included between the cycles of aspiration and delivery of the samples in which a flushing liquid is delivered through the tubular member. The samples are held in containers which are carried on a turntable which is indexed to place a desired sample container in position for the tubular member to aspirate a portion of the sample within the container and deliver it to the atomisation device. Between sample aspirations the turntable and a flushing discharge container are moved so that the flushing discharge container is positioned to take the discharge of flushing liquid from the tubular member. The flushing liquid is allowed to overflow the container and subsequently discharged to a drain. A disadvantage of this known apparatus is that it includes a relatively complex mechanism to move the turntable and flushing discharge container for each sample and flushing stage. The turntable is not merely rotated about its axis of rotation to perform this function but that the axis of rotation together with the turntable driving mechanism has to be moved.

It is an object of the invention to provide apparatus for automatically supplying liquid samples to an analytical instrument, which apparatus overcomes the above-mentioned disadvantage.

The invention provides an automatic liquid sample supply apparatus for sequentially supplying liquid samples to an analytical instrument comprising a plurality of sample containers carried on a turntable, a delivery tube movable between a first position within a container on the turntable and a second position at a sample input of the instrument, means for aspirating a predetermined volume of a sample from a sample container into the tube when in the first position, means for expelling the sample into the instrument when in the second position, and means for discharging a flushing liquid through the delivery tube when in the first position and the turntable is indexed so that the delivery tube enters a flushing discharge container characterised in that the flushing discharge container is carried by the turntable and is provided with an overflow aperture above the delivery end of the tube and below the lower surface of the turntable. Apparatus according to the invention enables flushing of the delivery tube without the necessity of moving the turntable or delivery tube laterally to a separate flushing position.

The flushing container in the apparatus described in the preceding paragraph may take the form of a sample container having an aperture formed in a side wall thus enabling the turntable to be manufactured with regularly spaced identical apertures for carrying both the sample and flushing discharge containers. The turntable may be enclosed by a cover having an aperture through which the delivery tube is inserted into the sample or flushing discharge container indexed to the first position and may be indexed to bring a flushing discharge container below the aperture after each sample aspiration. Since a series of measurements on a sample may take up to 30 minutes if the sample container is exposed to air for this period there is a risk of airborne dust contaminating the sample and hence being a source of error in the analysis. In order to reduce the number of steps through which the turntable has to be indexed to reach a flushing position from a given sample position two or more flushing discharge containers may be provided in diametrically opposite or in other predetermined positions on the turntable. In instruments such as atomic absorption spectrophotometers the analysis may be performed in a protective gas atmosphere in which case the protective gas supply may be used to pressurise the flushing liquid supply to force the flushing liquid through the delivery tube. A solenoid valve may be connected between the flushing liquid supply and the delivery tube, the valve being opened when the turntable is indexed to a flushing position.

The invention also provides a flushing discharge container suitable for use in an automatic liquid sample supply apparatus as described in either of the two preceding paragraphs, the container having bottom and side walls with the overflow aperture formed in a side wall, the aperture being so dimensioned that a flushing liquid within the container will not flow from the aperture unless a head of liquid is formed above the top of the aperture.

The container described in the preceding paragraph may be formed as a hollow cylinder closed at one end, the aperture being formed in the curved surface. The portion of the container adjacent of the closed end may be frustro conical. This will cause the liquid flowing through the aperture to drip from a relatively small diameter surface enabling the drain area to be kept relatively small and minimise the size of any residual drop carried by the container. A fully conical end, i.e. ending in a point, would be advantageous as far as directing the waste flow is concerned but would be more difficult to fabricate by injection moulding unless the interior also came to a point. Also this shape is not considered desirable as it may cause residues to be left in the container, requires a high degree of accuracy of placement of the delivery tube in the container and causes an increase in the overall depth of the container. In order to locate the container in an aperture in a turntable the open end may be provided with an outwardly extending flange. The container may then be merely dropped into an aperture in the turntable in the same way as sample containers. The aperture may be circular and have a diameter of between 3.5 mm and 4.5 mm. It has been found that if water is used as the flushing liquid it will flow in a steady stream out of an aperture 4.5 mm in diameter but will only flow out of a 4.0 mm aperture in discrete drops, provided that the flow rate is not so high such that a large head is formed above the top of the aperture. The minimum dimension for the hole depends on the height of the head above the top of the aperture which is desired or can be accommodated. The container may be formed as a polypropylene injection moulding.

The invention still further provides a method of flushing the delivery tube for liquid samples in an automatic liquid sample supply apparatus as described in the third or fourth preceding paragraphs incorporating a flushing discharge container as described in the first or second preceding paragraphs comprising the step of passing a flushing liquid along the tube and out of its delivery end at a flow rate determined in relation to the size of the aperture such that the flushing liquid flows from the aperture in discrete drops when a desired head above the aperture has been established. This causes a rise and fall in the flushing liquid inside the container which in turn causes a scrubbing action on the outside of the delivery tube thus increasing the efficiency of the cleaning action on the tube.

BRIEF DESCRIPTION OF THE DRAWINGS

An embodiment of the invention will now be described, by way of example, with reference to the accompanying drawings, in which.

Figure 1:
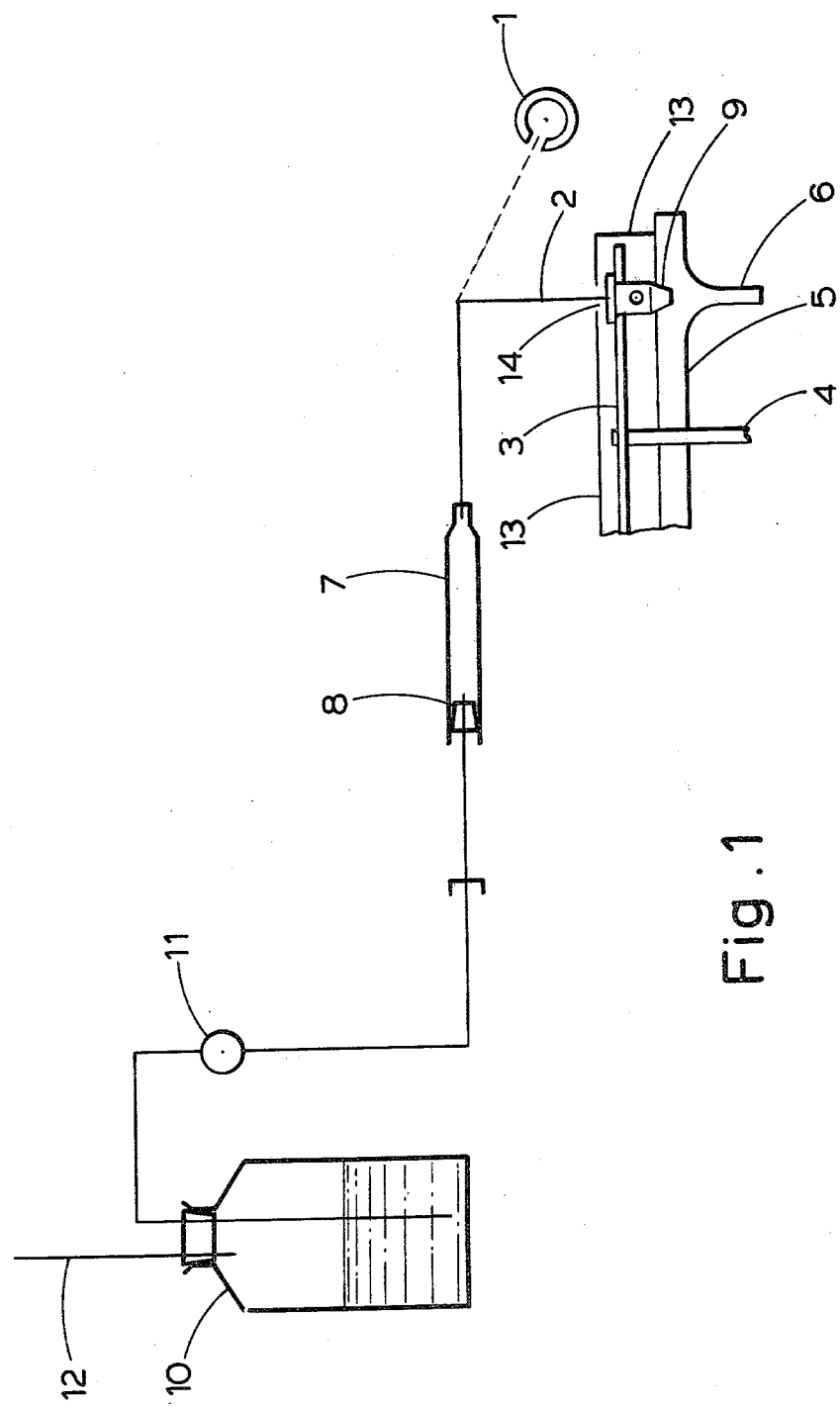
FIG. 1 shows schematically automatic sampling apparatus for an analytical instrument according to the invention.

The automatic sampling apparatus shown in FIG. 1 which may be used for delivering liquid samples into the dosing aperture of the graphite tube 1 of an atomisation device comprises a delivery tube 2 which is pivotable from a first position in which it enters sample containers on a turntable 3 to a second position at the dosing aperture of graphite tube 1. The turntable 3 is supported on a shaft 4 and is rotated by a motor (not shown) to index the turntable so that a desired sample container is positioned below the first position of the tube 2. A driptray 5 having an outlet 6 for connection to a drain is located beneath the turntable 3. The turntable 3 is enclosed by a cover 13 having an aperture 14 through which a selected container is accessible.

In operation the turntable is indexed to a desired position and the delivery tube 2 lowered into the sample container brought into alignment with the first position. A syringe 7 is then operated by withdrawing plunger 8 along the barrel of the syringe to aspirate a desired quantity of the sample into the tube 2. The tube 2 is then raised from the sample container pivoted and inserted into the dosing aperture of the graphite tube 1. The plunger 8 of the syringe 7 is then advanced along the barrel of the syringe to expel the sample from the delivery tube 2 into the graphite tube 1. The delivery tube 2 is then withdrawn from the dosing aperture of the graphite tube and pivoted back into position above the turntable. The delivery tube may now be re-inserted in the same sample container or the turntable may be indexed so that a flushing discharge container 9 is brought into alignment with the first position.

In order to reduce the possibility of airborne dust contaminating the samples in the sample containers the turntable may be indexed to bring the flushing discharge container below the aperture 14 after each sample aspiration. The delivery tube is preferably flushed after each sample delivery but if repeated measurements of samples from the same sample container are to be made the flushing operation may be omitted. This does however increase the risk of contamination of the tip of the delivery tube by airborne dust. The cover 13 also provides a closed space around the turntable thereby reducing the rate of evaporation of the sample.

Figure 4:
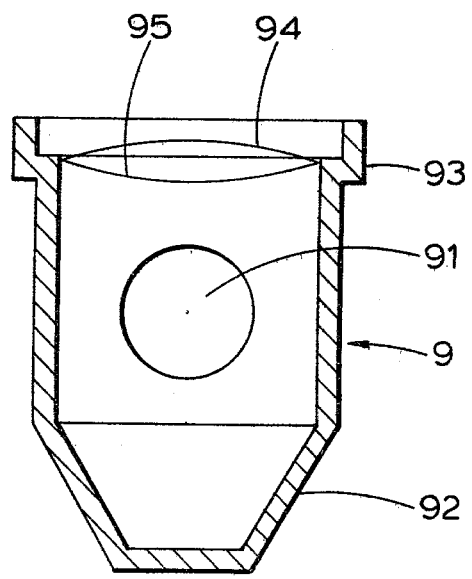
FIG. 4 is a cross sectional elevation of a flushing discharge container according to the invention.

When the turntable is indexed so that the flushing discharge container 9 is aligned with the first position, the delivery end of the tube 2 is then lowered into it and a flushing liquid is passed from a flushing liquid supply container 10 via a solenoid valve 11, the syringe 7 and the tube 2 through the delivery end of the tube into the flushing discharge container 9. The flushing liquid supply container 10 is pressurised via a tube 12 which may be connected to an inert gas supply cylinder which is also used to provide a non-oxidising atmosphere for the graphite tube. As can be seen more clearly in FIG. 4 the flushing discharge container 9 comprises a cup like body having an aperture 91 in its side wall. It is generally cylindrical but a frustro-conical portion 92 is provided below the aperture 91 and an outwardly extending flange 93 is provided at the top of the cylindrical wall. The external surface of frustro-conical portion 92 limits the area over which liquid discharged from aperture 91 falls and the internal surface allows the flow of flushing liquid from the end of the delivery tube to scour the inside of the container. An external point would be more effective in directing the liquid discharge but when the container is injection moulded it is desirable to keep a constant wall thickness. It is not desirable for the internal surface to come to a point as it would not be easy to lower the delivery tube to the bottom of a pointed container due to the accuracy of placement required. If the delivery tube is not lowered to the bottom of the tube the scouring action may be reduced and sample carry-over may occur. Further this would increase the total depth of the container 9 and require a greater spacing between the turntable 3 and driptray 5.

The sample containers have the same form as the flushing discharge container 9 except that the aperture 91 is not present. Hence both types of container can be accommodated in the same sized holes in the turntable 3 and are located by the flange 93. The aperture 91 in the flushing discharge container is placed as far up the wall as possible commensurate with the top of the aperture 91 being below the lower surface of the turntable 3. The sample containers are designed to take a 500 μL sample which brings the level of sample in the container to a level equivalent to the top of the aperture 91 in the flushing discharge container 9 thus in order to ensure that carry over of samples is minimised it is necessary to ensure that the flushing liquid fills the flushing discharge container to above that level. By dimensioning the aperture so that the flushing liquid will not flow through it until a head of liquid above the aperture is established it can be ensured that the necessary length of the outside of the delivery tube 2 is cleaned.

For a nominal 500 μL sample containers have been designed that have an outside diameter of 10 mm and a total height of 15 mm with a wall thickness of 0.8 mm. The aperture 91 in the flushing discharge container 9 is made 4 mm in diameter and centered 6.2 mm from the top of the container. This means that the top of the aperture 91 corresponds to the surface level of a 500 µL sample in the sample containers.

It has been found experimentally that with a 4 mm aperture 91 and water as the flushing liquid the flow from the aperture 91 is in discrete drops at least with flow rates up to 10 mL per minute through a 1.2 mm outside diameter delivery tube. Observations have shown that a convex meniscus 94 is formed prior to drop formation and that as the drop leaves the hole the meniscus drops in the centre to form a concave meniscus 95 which then builds up to the convex meniscus 94 as liquid flows from the tube 2 into the container 9 until a further drop forms and is discharged from aperture 91, the process continually repeating itself. The mechanism of drop formation appears to be independent of the flow rate provided it does not exceed the maximum rate of discharge from the aperture 91. The speed of drop formation, of course, depends on the flow rate. It was found that if the diameter of the aperture 91 was reduced to 3.5 mm the increased head required for drop formation caused the convex meniscus 94 to extend above the top surface of the container. However, when methylisobutylketone (mibk) was used as the flushing liquid the meniscus formed with a 3.5 mm aperture was approximately the same as that formed with a 4 mm aperture when water is used as a flushing liquid. The rise and fall of the meniscus as the drops form produces a scrubbing action on the outside of the delivery tube and consequently increases the efficiency of the cleaning action on the tube.

Figure 2:
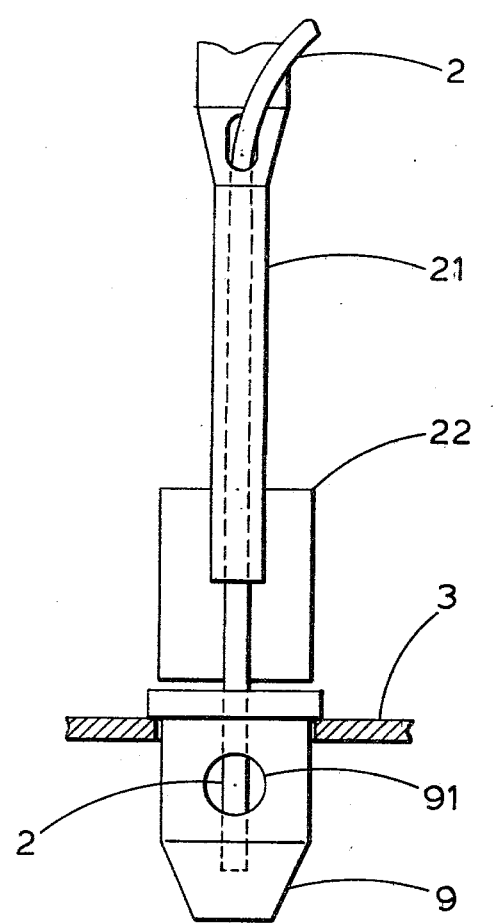
FIG. 2 shows on an enlarged scale the sample delivery tube and flushing discharge container shown in FIG. 1.

Since the dosing aperture of the graphite tube 1 has a small diameter and the sample and flushing discharge containers are small it is desirable that the free length of the delivery tube 2, which may be a p.t.f.e. tube, should be kept as small as possible. As shown in FIG. 2 the delivery tube 2 is passed through a stainless steel shuttle 21 and clamped by a clamp 22. The free length of tubing protruding from the clamp for use with the size of sample cups outlined hereinbefore is made about 12 mm and the shuttle assembly is connected to a pivot assembly which serves to move the delivery end of the tube between the first and second positions. When the tube is in the first position the shuttle 21 is lowered so that the end of the tube 2 enters the sample or flushing discharge container indexed under it by the turntable 3. The gap between the bottom of the clamp 22 and the top of the sample or flushing discharge container 9 is made as small as possible so that the tube 2 penetrates well into the container. It is, therefore, important that the meniscus 94 formed by the flushing liquid should not protrude above the top of the container otherwise droplets could be formed on the clamp 22 and subsequently transferred to the graphite tube or the next sample container.

Figure 3:
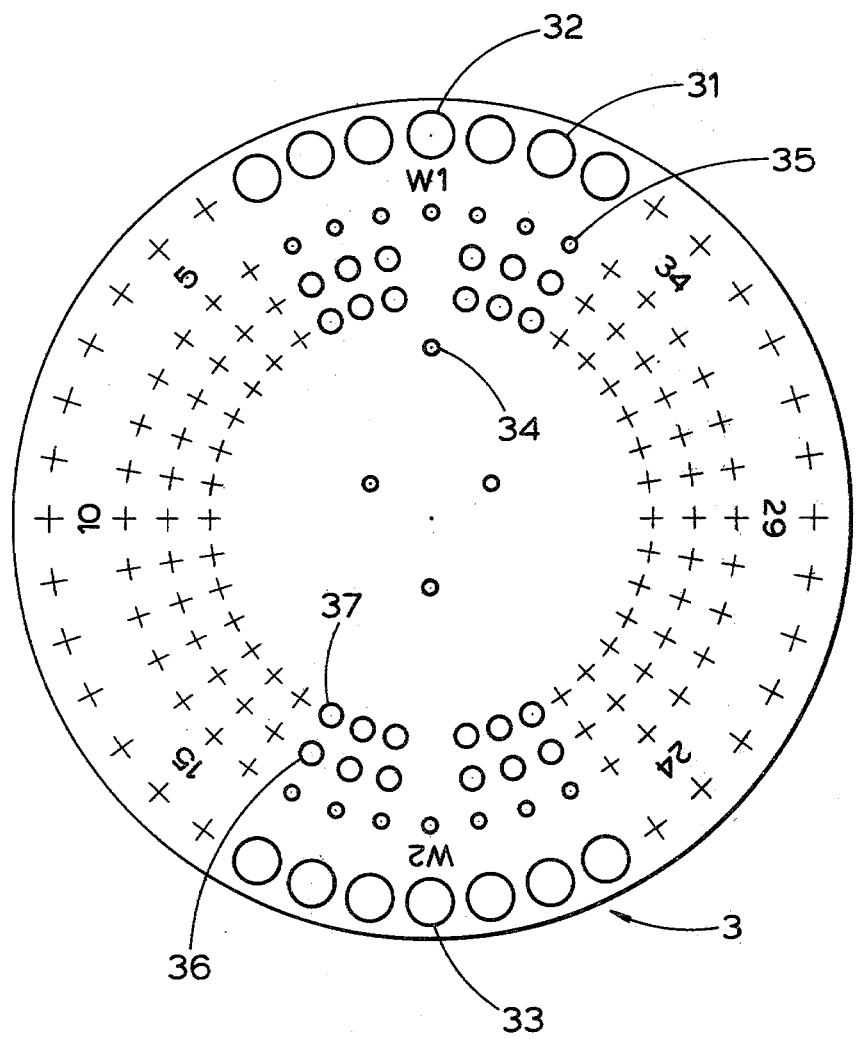
FIG. 3 is a plan view of the turntable of FIG. 1.

The turntable is shown in greater detail in FIG. 3 and comprises a circular disc 3 having appropriately placed apertures. Forty 10.4 mm diameter holes, one of which is shown at 31, are provided at regular intervals to accommodate the sample and flushing discharge containers. Two flushing discharge containers are located at diametrically opposite positions 32 and 33. A hole 34 is provided on a radius on which the hole 32 is centered to mark a reference position for the turntable. A sensor is used to detect that hole 34 is in a preset position at the start of operations and movement of the turntable is referenced to the preset position. A further series of holes 35 are provided to enable sensing devices to determine that the turntable is indexed with the desired container below the first position of the tube 2. Two further series of holes 36 and 37 enable encoding of the analytical function to be performed on the particular sample. The encoding is activated by either opening or blocking the hole in each series associated with the sample position.

While the invention has been described in relation to the automatic injection of samples into the dosing aperture of a graphite tube of an atomisation device it could be applied in other fields for example liquid chromatography. More than two flushing discharge containers may be provided at predetermined intervals around the turntable. The number of flushing discharge containers is chosen as the best compromise between reducing the number of sample positions available and increasing the average number of steps through which the turntable has to be indexed to reach a flushing position from a given sample position.

I claim:

1. An automatic liquid sample supply apparatus for sequentially supplying liquid samples to an analytical instrument comprising a plurality of sample containers carried on a turntable, a delivery tube movable between a first position within a container on the turntable and a second position at a sample input of the instrument, means for aspirating a predetermined volume of a sample from a sample container into the tube when in the first position, means for expelling the sample into the instrument when in the second position, and means for discharging a flushing liquid through the delivery tube when in the first position and the turntable is indexed so that the delivery tube enters a flushing discharge container, characterised in that the flushing discharge container is carried by the turntable and is provided with an overflow aperture above the delivery end of the tube and below the lower surface of the turntable.

2. Apparatus as claimed in claim 1 in which the flushing container has the form of a sample container with an aperture formed in a side wall and the turntable has regularly spaced identical apertures for carrying both the sample and flushing discharge containers.

3. Apparatus as claimed in claim 1 or claim 2 in which the turntable is enclosed by a cover having an aperture through which the delivery tube is inserted into the sample or flushing discharge container indexed to the first position.

4. Apparatus as claimed in claim 1 in which two or more flushing discharge containers are provided in predetermined positions on the turntable.

5. Apparatus as claimed in claim 1 in which the analysis is performed in a protective gas atmosphere and the gas supply pressurises the flushing liquid supply to force the flushing liquid through the delivery tube.

6. A flushing discharge container suitable for use in an automatic liquid sample supply apparatus, said container having bottom and side walls and an overflow aperture formed in a side wall, said aperture being so dimensioned that a flushing liquid within said container will not flow from said aperture unless a head of liquid is formed above the top of said aperture.

7. A container as claimed in claim 6, wherein said container is formed as a hollow cylinder closed at one end, the portion of the container adjacent to the closed end being frusto-conical and said aperture being formed in the curved surface.

8. A container as claimed in claim 6, wherein said container is formed as a hollow cylinder closed at one end, and said aperture is formed in the curved surface, and wherein the open end is provided with an outwardly extending flange.

9. A container as claimed in one of claim 6, or claim 7 or claim 8 in which said aperture is circular and has a diameter between 3.5 mm and 4.5 mm.

10. A method of flushing the delivery tube for liquid samples in automatic liquid sample supply apparatus incorporating a flushing discharge container having a discharge aperture comprising the step of passing a flushing liquid along the tube and out of its delivery end at a flow rate determined in relation to the size of the aperture such that the flushing liquid flows from the aperture in discrete drops when a desired head above the aperture has been established.

11. Apparatus as claimed in claim 3 in which the flushing discharge container is placed below said aperture after each sample aspiration.

12. Apparatus as claimed in claim 1 in which a solenoid valve is connected between the flushing liquid supply and said delivery tube, said valve being opened when said turntable is indexed to a flushing position.

13. Apparatus as claimed in claim 1 in which said analytical instrument is an atomic absorption spectrometer.

14. A method as claimed in claim 10 in which said flushing liquid flows from said aperture in discrete drops.

15. A method as claimed in claim 10 in which said flushing liquid flows from said aperture at a flow rate of up to 10 ml/min.

16. A method as claimed in claim 10 in which said flushing liquid is water.

17. A method as claimed in claim 10 in which said flushing liquid is an organic fluid.

* * * * *